(12) United States Patent
Fielding et al.

(10) Patent No.: US 8,554,368 B2
(45) Date of Patent: Oct. 8, 2013

(54) FRAME MAPPING AND FORCE FEEDBACK METHODS, DEVICES AND SYSTEMS

(76) Inventors: Tim Fielding, Brampton (CA); Perry Newhook, Caledon (CA)

( * ) Notice: Subject to any disclaimer, the term of this patent is extended or adjusted under 35 U.S.C. 154(b) by 680 days.

(21) Appl. No.: 12/596,417

(22) PCT Filed: Apr. 16, 2008

(86) PCT No.: PCT/IB2008/003363
§ 371 (c)(1),
(2), (4) Date: Mar. 30, 2010

(87) PCT Pub. No.: WO2009/034477
PCT Pub. Date: Mar. 19, 2009

(65) Prior Publication Data
US 2011/0160745 A1 Jun. 30, 2011

Related U.S. Application Data

(60) Provisional application No. 60/912,144, filed on Apr. 16, 2007.

(51) Int. Cl.
*G05B 19/04* (2006.01)

(52) U.S. Cl.
USPC .......... 700/247; 700/245; 700/248; 700/251; 700/256; 700/259; 700/261; 700/264

(58) Field of Classification Search
USPC ................ 700/245, 247, 248, 251, 256, 259, 700/261, 264; 901/2, 5, 8, 9, 14, 16, 20, 901/46, 47
See application file for complete search history.

(56) References Cited

U.S. PATENT DOCUMENTS

| 4,831,549 | A | * | 5/1989 | Red et al. | 700/254 |
| 4,833,381 | A | * | 5/1989 | Taft et al. | 318/577 |
| 4,843,287 | A | * | 6/1989 | Taft | 318/568.16 |
| 5,542,180 | A | * | 8/1996 | Karani | 30/134 |
| 5,815,640 | A | * | 9/1998 | Wang et al. | 700/251 |
| 5,876,325 | A |   | 3/1999 | Mizuno et al. | 600/102 |
| 6,522,906 | B1 | * | 2/2003 | Salisbury et al. | 600/407 |

(Continued)

FOREIGN PATENT DOCUMENTS

| EP | 592 681 | 4/1994 |
| EP | 1 791 070 | 5/2007 |

(Continued)

OTHER PUBLICATIONS

International Preliminary Report on Patentability sued in International Application No. PCT/IB2008/003363, dated Jan. 5, 2010.

(Continued)

*Primary Examiner* — Khoi Tran
*Assistant Examiner* — Jorge Peche
(74) *Attorney, Agent, or Firm* — Fulbright & Jaworski LLP

(57) ABSTRACT

Methods, devices, and systems for controlling movement of a slave manipulator by an operator controlling a master manipulator in a way that the motion of that slave manipulator can be presented via a display to the operator such that the displayed position of the slave manipulator is intuitive to the operator, regardless of the actual position and orientation of the slave manipulator. Methods, devices, and systems relating to force feedback associated with medical robotic procedures.

19 Claims, 14 Drawing Sheets

(56) References Cited

U.S. PATENT DOCUMENTS

| | | | |
|---|---|---|---|
| 6,810,281 B2 * | 10/2004 | Brock et al. | 600/427 |
| 6,822,412 B1 * | 11/2004 | Gan et al. | 318/568.19 |
| 6,898,484 B2 * | 5/2005 | Lemelson et al. | 700/245 |
| 7,107,090 B2 * | 9/2006 | Salisbury et al. | 600/427 |
| 7,155,315 B2 | 12/2006 | Niemeyer et al. | 700/245 |
| 7,155,316 B2 * | 12/2006 | Sutherland et al. | 700/248 |
| 7,395,606 B2 * | 7/2008 | Crampton | 33/503 |
| 7,962,192 B2 * | 6/2011 | Bodduluri et al. | 600/407 |
| 7,996,110 B2 * | 8/2011 | Lipow et al. | 700/245 |
| 2002/0055795 A1 | 5/2002 | Niemeyer et al. | 700/90 |
| 2003/0208302 A1 * | 11/2003 | Lemelson et al. | 700/245 |
| 2004/0251866 A1 * | 12/2004 | Gan et al. | 318/568.11 |
| 2005/0166413 A1 * | 8/2005 | Crampton | 33/503 |
| 2007/0106306 A1 * | 5/2007 | Bodduluri et al. | 606/133 |
| 2007/0106307 A1 * | 5/2007 | Bodduluri et al. | 606/133 |
| 2008/0027580 A1 * | 1/2008 | Zhang et al. | 700/245 |
| 2008/0201016 A1 * | 8/2008 | Finlay | 700/259 |
| 2008/0235970 A1 * | 10/2008 | Crampton | 33/503 |
| 2009/0171371 A1 * | 7/2009 | Nixon et al. | 606/130 |

FOREIGN PATENT DOCUMENTS

| | | |
|---|---|---|
| GB | 2 235 067 | 2/1991 |
| WO | WO 95/07055 | 3/1995 |
| WO | WO 01/62173 | 8/2001 |

OTHER PUBLICATIONS

International Search Report issued in International Application No. PCT/IB2008/003363, dated Feb. 4, 2010.
Written Opinion issued in International Application No. PCT/IB2008/003363, dated May 11, 2009.
Hiatt, et al., "Coordinate Frames in Robotic Teleoperation", Intelligent Robots and Systems, 2006 IROS, Oct. 1, 2006, pp. 1712-1719, XP031006333.

* cited by examiner

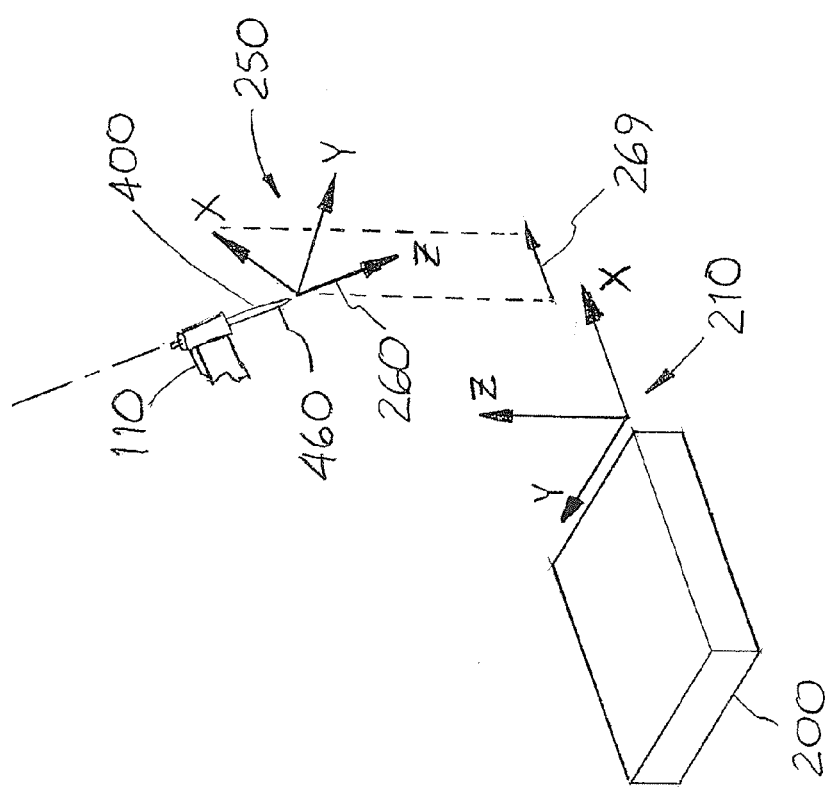
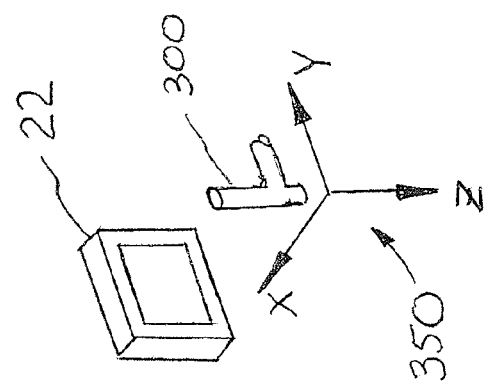
FIG. 6

FRAME MAPPING AND FORCE FEEDBACK METHODS, DEVICES AND SYSTEMS

CROSS REFERENCE TO RELATED APPLICATIONS

This application is a national phase application under 35 U.S.C. §371 of International Application No. PCT/IB2008/003363, filed Apr. 16, 2008, which claims priority to U.S. Provisional Patent Application Ser. No. 60/912,144, filed Apr. 16, 2007, the entire contents of each of which are incorporated by reference.

BACKGROUND

The present methods, devices, and systems relate generally to the field of surgical robotics, and more particularly to techniques for controlling movement of a slave manipulator by an operator controlling a master manipulator in a way that the motion of that slave manipulator can be presented via a display to the operator such that the displayed position of the slave manipulator is intuitive to the operator, regardless of the actual position and orientation of the slave manipulator. The present methods, devices, and systems also relate to force feedback systems. An example of a surgical robot that can be used in a procedure to which the present methods, devices, and systems relate is disclosed in U.S. Pat. No. 7,155,316 (the "'316 patent"), which is incorporated by reference.

SUMMARY

In a broad respect, the present techniques relate to controlling the movement of a slave manipulator (e.g., a robotic arm having multiple degrees of freedom, such as the robotic arms disclosed in the '316 patent) as commanded by an operator through a master manipulator, or controller device, in such a way that, if the operator commands the slave manipulator to move by manipulating the master manipulator as he or she is viewing the actual movement of the slave manipulator through a display, the slave manipulator moves in such a way that the display of its movement to the operator is intuitive, regardless of the actual position and orientation of the slave manipulator relative to the actual position and orientation of the master manipulator, the position and orientation of the slave manipulator being independent of the position and orientation of the master manipulator at any given time, and the display being at a location that does not correspond to the actual location from which the information displayed is located (e.g., the operator views the slave manipulator via a stereoscopic display of the slave manipulator taken using a stereoscopic camera system positioned in another room next to the slave manipulator (which is in the other room)). Controlling slave manipulator movement in this way gives the operator an intuitive feel for the slave manipulator's movement, regardless of the actual position and orientation of the slave manipulator relative to the operator and/or the master manipulator the operator is manipulating. For example, the operator sees the slave manipulator (or manipulators if there are multiple master manipulators) holding an instrument (a surgical tool for example) in the display in the same relative position and orientation as if the operator was holding the tool under the actual microscope taking the displayed image(s).

Thus, some embodiments of the present techniques are embodied in a control system configured for use with at least one medical robotic arm, the control system being configured to perform at least the following: determine a calculated motion of a tool of the medical robotic arm, where: the determining of the calculated motion is based on an input value received from a controller device that provides input from a user; and the calculated motion is expressed in an observer coordinate system that is based on the orientation of the tool and the orientation of an observer reference structure; and output an actuation signal to move the medical robotic arm in accordance with the calculated motion. The actuation signal may be any suitable form of data that includes information sufficient to cause the medical robot arm to move appropriately. For example, the actuation signal could represent a set of joint displacements and/or joint velocities output by the control system to a medical robotic arm's local controller, or directly to the individual joint actuators.

The present techniques also relate to providing force feedback to the operator in an intuitive manner. The force feedback may be derived from actual forces measured at the slave manipulator (such as tooltip forces), or from virtual forces that may be programmed by an operator or that may exist as a result of limitations on the joints of the slave manipulator (including velocity limits and joint angle limits), or from a combination of actual forces and virtual forces. The actual forces may be measured by a slave manipulator that is configured for measuring tooltip forces by coupling the surgical tool to the end effector through force sensors and a flexible coupling. The flexible coupling may facilitate actuation of the surgical tool without providing the tooltip forces with a load path that bypasses the force sensors. For example, the flexible coupling may be configured to be compliant in all directions except for rotation about its center axis, and therefore does not transmit any component of a tooltip force to the robotic arm (e.g., through an end effector of the robotic arm). As a result, the entirety of a given tooltip force may be balanced by forces acting through the force sensors, and calculation of that tooltip force may be accomplished from the values measured by the force sensors.

Any embodiment of any of the present methods, devices (e.g., computer readable media), and systems (e.g., computer systems, such as control systems) may consist of or consist essentially of—rather than comprise/include/contain/have—the described functions, steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE DRAWINGS

The following drawings illustrate by way of example and not limitation. Identical reference numerals do not necessarily indicate an identical structure, system, or display. Rather, the same reference numeral may be used to indicate a similar feature or a feature with similar functionality. Every feature of each embodiment is not always labeled in every figure in which that embodiment appears, in order to keep the figures clear. The controller devices, manipulators, and tools shown in the figures are drawn to scale, meaning the sizes of the depicted elements are accurate relative to each other.

FIG. 6 is a schematic illustration showing several coordinate systems related to the present embodiments.

DESCRIPTION OF ILLUSTRATIVE EMBODIMENTS

Figure 1:
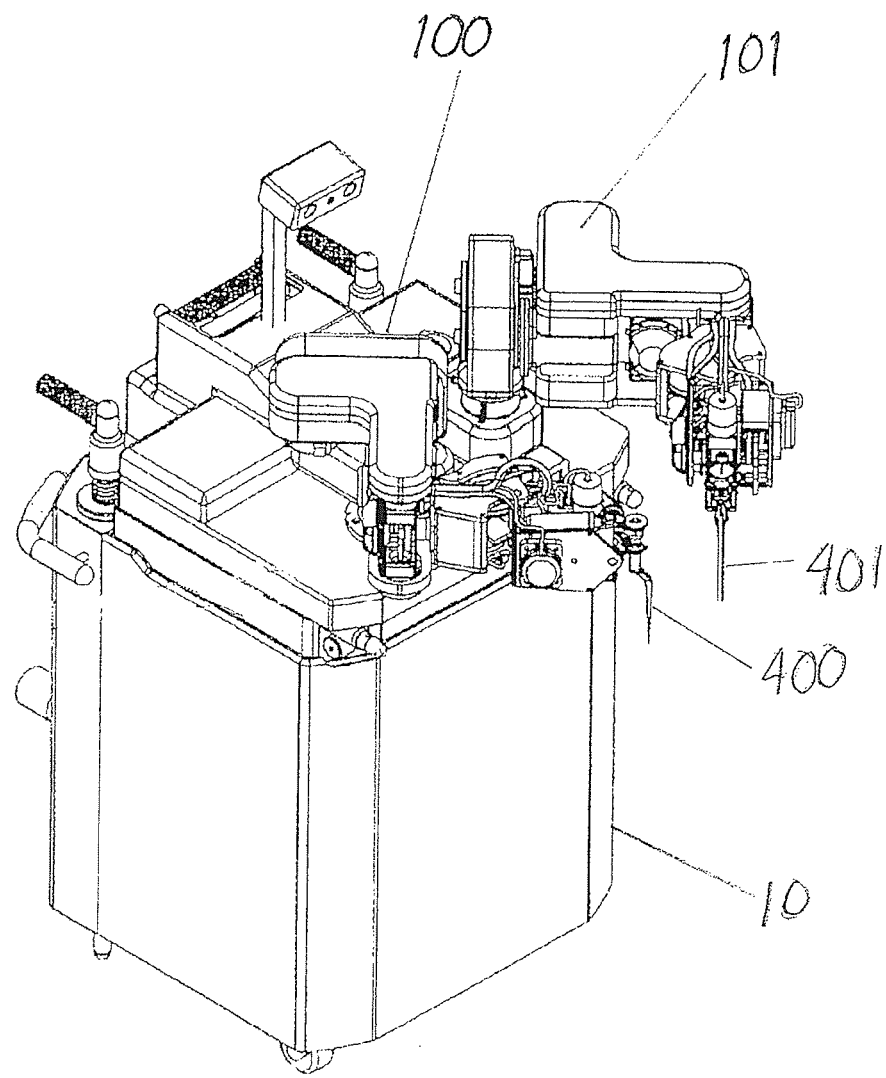
FIG. 1 is a perspective view of a medical robotic system suitable for use with the present embodiments.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. Thus, a method comprising certain steps is a method that includes at least the recited steps, but is not limited to only possessing the recited steps. Similarly, a computer readable medium "comprising" machine readable instructions for performing certain steps is a computer readable medium that has machine readable instructions for implementing at least the recited steps, but also covers media having machine readable instructions for implementing additional, unrecited steps. Further, a computer system that is configured to perform at least certain functions is not limited to performing only the recited functions, and may be configured in a way or ways that are not specified provided the system is configured to perform the recited functions.

The terms "a" and "an" are defined as one or more than one, unless this application expressly requires otherwise. The term "another" is defined as at least a second or more.

In some embodiments, a surgical robot such as the one disclosed in the '316 patent can be controlled by an operator who uses a virtual microscope display showing the image of the surgical scene as viewed from the microscope. The operator controls the manipulators (the robotic arms of the robot) in that scene through the use of two hand controllers that are situated coincident with the virtual microscope view. The effect is that the operator sees the manipulators holding the surgical tools in the virtual microscope view in the same relative position and orientation as if the surgeon was holding them under the real microscope.

In such embodiments, to obtain intuitive control of a given manipulator by the surgeon, the manipulator must respond to operator input in a direction that mimics the motion the surgeon (the operator) makes with his hands. If the surgeon pushes his hands away from his body, he would expect the manipulator in the microscope view to also move away in the same visual direction. Since this visual point of view does not map directly to any physical reference frame on the manipulator, a virtual observer reference frame is created to map what the operator expects into what the manipulator executes. This reference frame mapping allows the hand controller stylus and surgical tool to be independently oriented while keeping the motion of the tool intuitive to the operator. The goals to create an intuitive mapping are that: (a) stylus motions directly toward and away from the user result in tool motions directly toward and away from the base to which the robotic arms are coupled during a procedure (aka, the "robot base"); and (b) stylus motions directed along the axis of the stylus result in tool motions along the axis of the tool. The determination of transformations that may be used in accomplishing the present frame mappings can be achieved through any suitable process, including through the registration process disclosed in co-pending International Application No. PCT/US08/60538, which is incorporated by reference.

In such embodiments, the virtual observer frame has a positive X axis that is always pointing directly away from the robot base, and which appears to the operator as pointing directly away from himself in the virtual microscope frame. The positive Z axis of the hand controller reference frame is directed along the handcontroller stylus axis, from back end of the stylus to the tip. The positive Z axis of the tool is along the tool axis directed from the tool holder to the tip; hence, a motion solely along the Z axis of the stylus creates a motion solely along the Z-axis of the tool.

In such embodiments, the virtual observer frame reference axis 'X' is defined as always pointing away from the operator, and this lines up as a direction that goes from bottom to top of the microscope image shown to the operator. Effectively, the observer frame is a virtual frame aligned to the tool axis on the manipulator end effector that has the following characteristics: 'Z', which is mapped to the stylus axis on the hand controllers is defined along the length of the tool; 'X', which is mapped as described above (away from the operator) defined at the tool tip in a direction such that the projection of that axis as viewed from above aligns with the 'X' axis of the microscope view at all times; and the 'Y' axis follows from right hand rule coordinate frame. This virtual observer frame is therefore the tool tip frame, but rotated about the tool Z axis such that the projection of the tool X axis on the robot base X-Y plane aligns with the robot base X axis. As the manipulator moves, this virtual observer frame is frequently if not constantly updated to keep the X axis aligned with the microscope camera X axis. This frame is independent of the orientation of the tool and manipulator, or the orientation of the tool frame. The result is that the hand controller commands in X and Y in the camera observer frame, always result in the intended X and Y motions as seen in the microscope camera image, and Z movement of the stylus will always be along the tool axis.

1.0 Observer Frame Mapping

The following explanation pertains to an example of how to implement embodiments of the present frame mapping techniques suitable for use with the type of surgical robot disclosed in the '316 patent.

FIG. 1 shows a robotic system suitable for use with the present frame mapping techniques. Medical robotic arm 100 and second medical robotic arm 101 are mounted to a common base, system base 10. Each robotic arm may have a tool (which may also be characterized as an instrument) that is suitable for use in medical (e.g., surgical) procedures.

Figure 2:
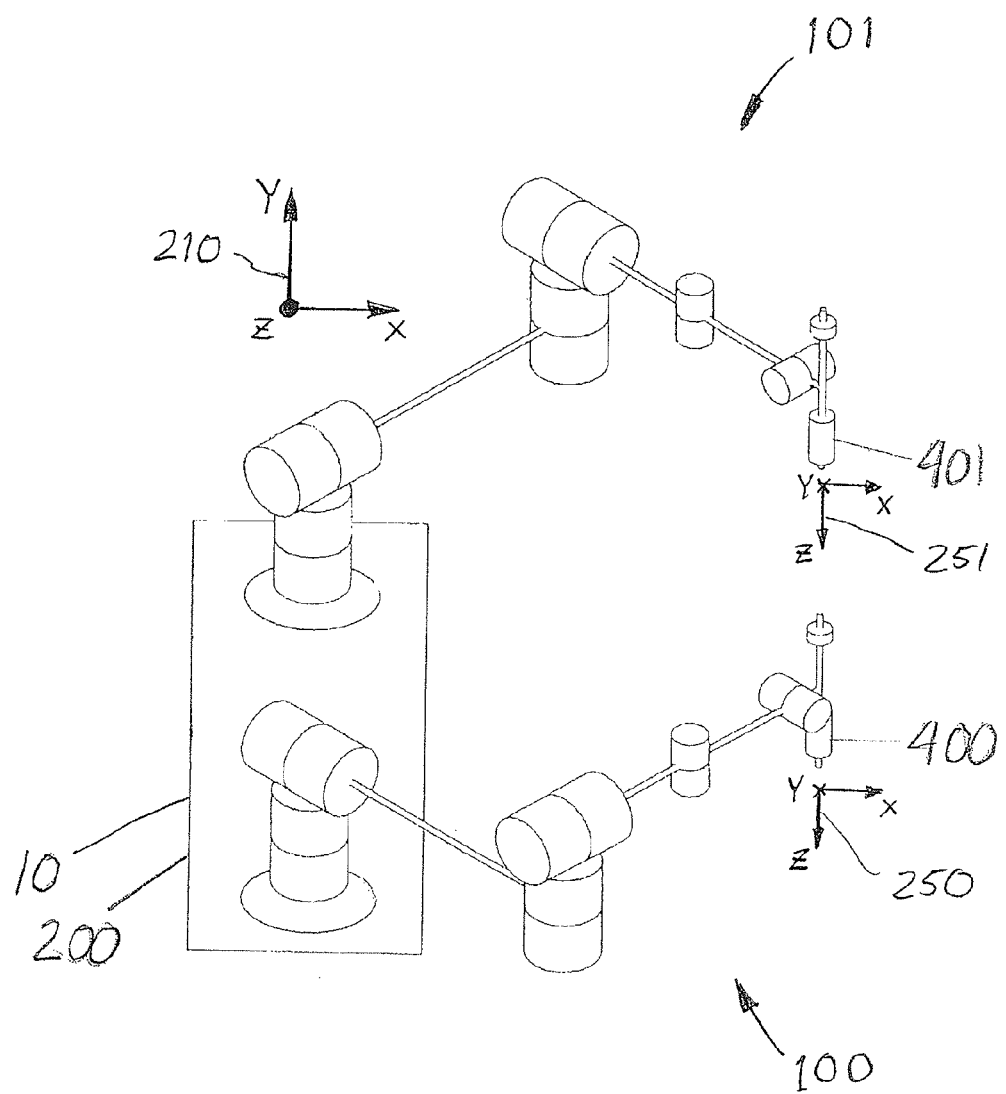
FIG. 2 is a schematic illustration of the robotic system of FIG. 1. Several coordinate systems related to the present embodiments.
Figure 14:
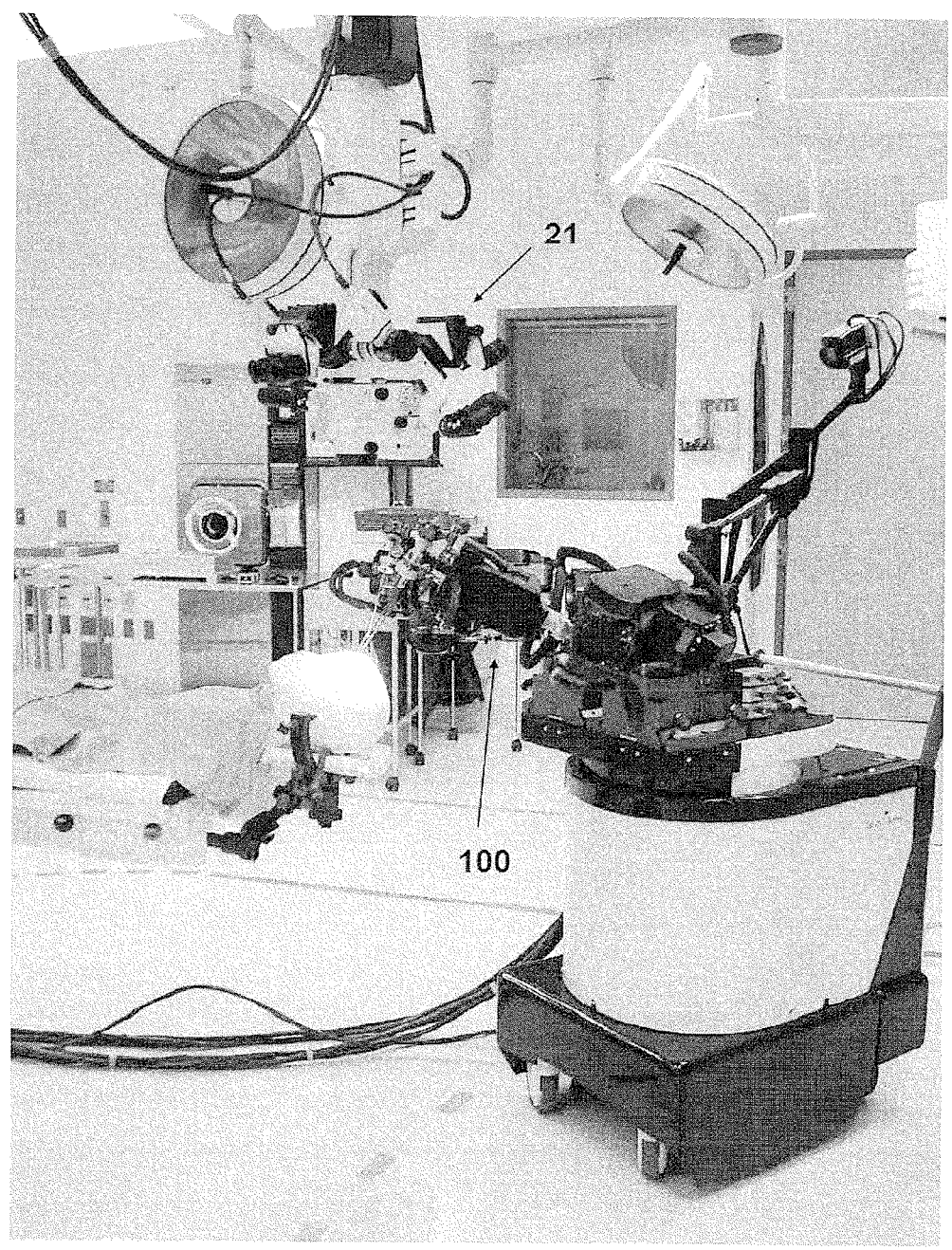
FIG. 14 illustrates a typical placement of an overhead camera and a medical robotic arm suitable for use with the present methods, devices, and systems.

FIG. 2 shows several coordinate systems related to the present embodiments. Observer reference structure 200 may be any structure that remains fixed (such as for the duration of a medial procedure) to the orientation of the image presented to the remote operator. That is, any structure that will be fixed relative to the overhead camera that provides the operator the image used during the medical procedure may serve as observer reference structure 200. In the embodiment depicted in FIGS. 1 and 2, system base 10 remains fixed relative to the orientation of camera 21 and therefore is a suitable observer reference structure 200. FIG. 14 illustrates overhead camera 21, which may be a stereoscopic camera, positioned over a patient that is undergoing a procedure performed by medical robotic arm 100. Other suitable observer reference structures 200 include overhead camera 21 and structures that are attached to the overhead camera 21.

The orientation of reference structure coordinate system 210 is fixed to the orientation of observer reference structure 200 and selected such that it has an X-axis that is generally horizontal, and oriented to point towards the region of the patient where the surgical procedure takes place. This region of interest remains generally fixed in location relative to observer reference structure 200 during the surgical procedure. Such an orientation results in a correlation between the X-axis of reference structure coordinate system 210 and the image presented to the operator by overhead camera 21. The orientation is selected such that the X-axis of reference structure coordinate system 210 corresponds to the vertical axis of the image, with the +X direction pointing to the top of the image. The Z-axis is selected to point up, and the resulting Y-axis direction follows convention for right-handed coordinate systems.

Figure 11:
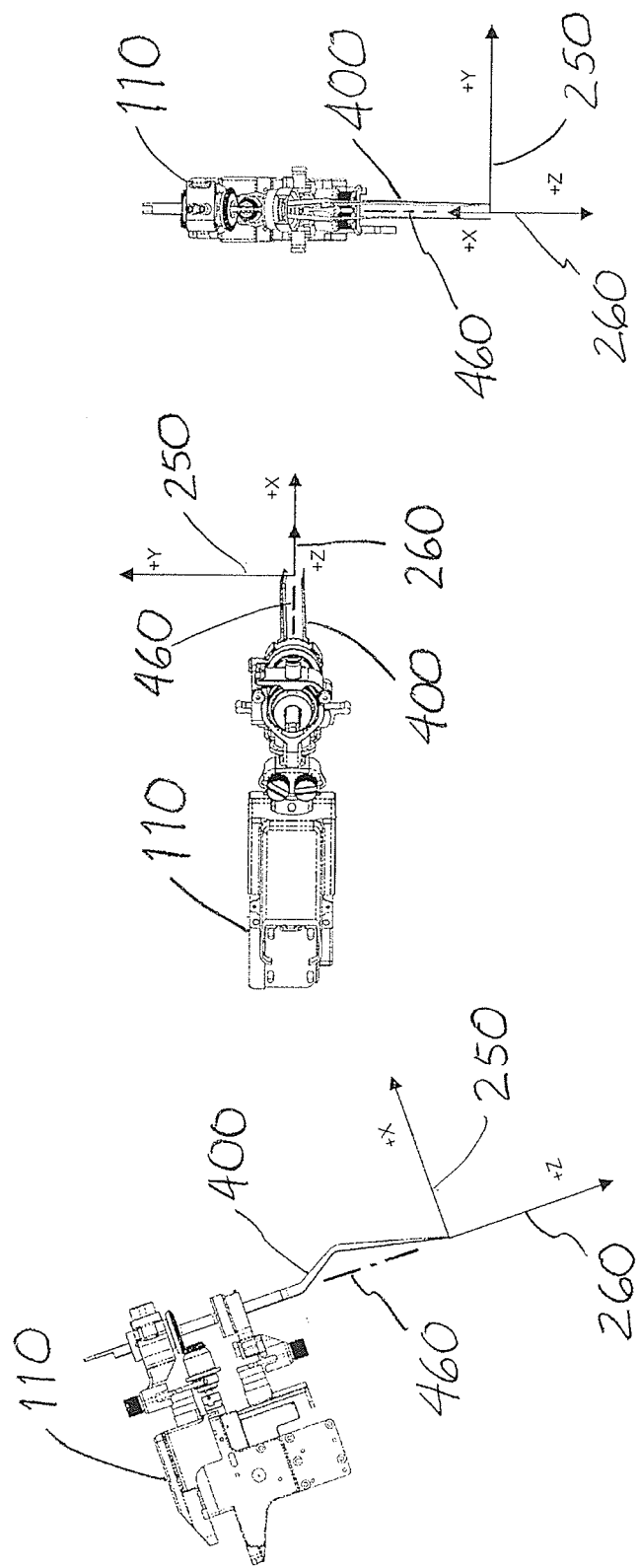
FIG. 11 depicts side, top, and end views of the end effector of a medical robotic arm suitable for use with the present embodiments. The end effector is holding a tool.

The orientation of observer coordinate system 250 is determined from the orientation of tool 400 and the orientation of observer reference structure 200. In some embodiments, the Z-axis of observer coordinate system 250 is aligned to tool axis 460 of tool 400, and the X-axis of observer coordinate system 250 is aligned such that its projection in the X-Y plane of reference structure coordinate system 210 is parallel to and pointing in the same direction as the X-axis of reference structure coordinate system 210. FIG. 6 illustrates observer coordinate system 250 oriented such that it has (1) a Z-axis that is aligned with tool axis 460, and (2) an X-axis that has projection 269 in the X-Y plane of reference structure coordinate system 210 that is parallel to and pointing in the same direction as the X-axis of reference structure coordinate system 210. The resulting Y-axis direction of observer coordinate system 250 follows convention for right-handed coordinate systems. FIGS. 7-11 further illustrate the alignment of observer coordinate system 250. FIG. 11 depicts side, top, and end views of the end effector 110 of a medical robotic arm, tool 400, tool axis 460, and coordinate system 250 having axis 260 aligned to tool axis 460.

Figure 8:
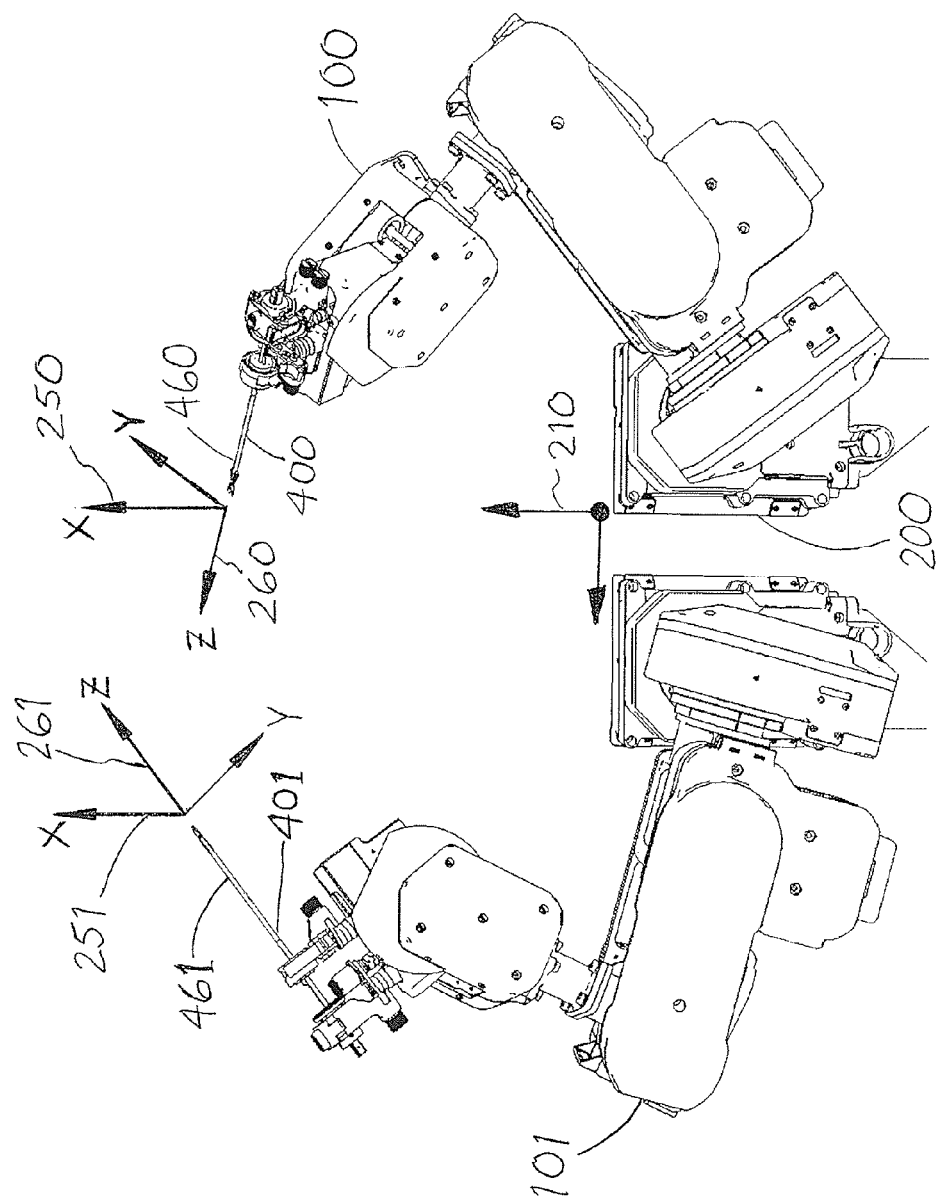
FIG. 8 is an overhead view of a dual-arm medical robotic system suitable for use with the present embodiments, depicting the alignment of the corresponding observer coordinate systems.
Figure 9:
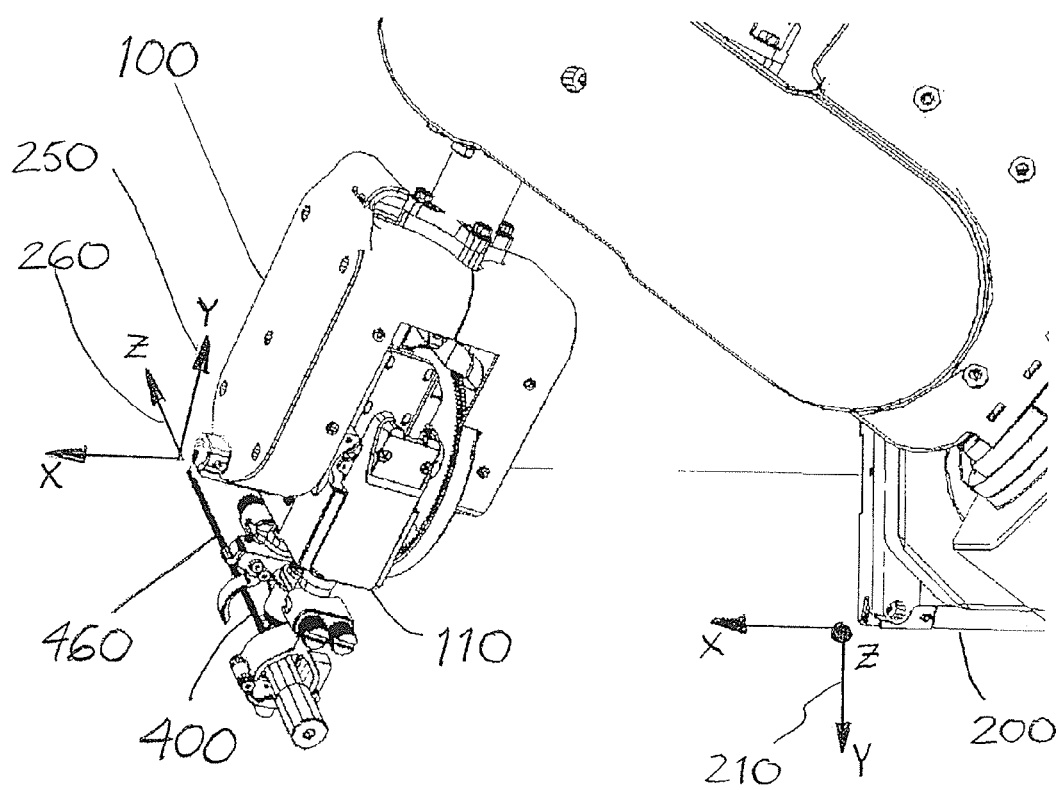
FIG. 9 is a overhead view of a medical robotic arm suitable for use with the present embodiments, depicting the alignment of the observer coordinate system.
Figure 10:
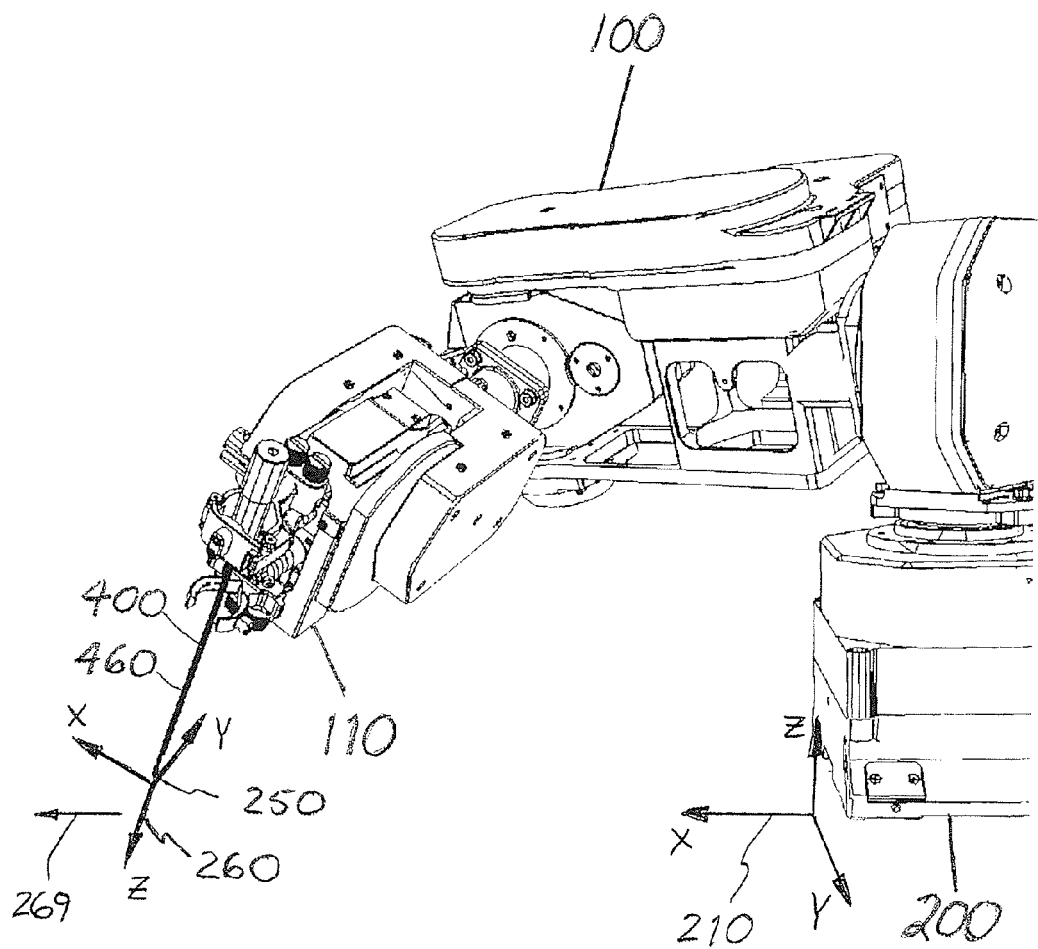
FIG. 10 is a perspective view of a medical robotic arm suitable for use with the present embodiments, depicting the alignment of the observer coordinate system.

In systems that include multiple robotic arms working concurrently, such as those suitable for use in microscopic surgical procedures, each robotic arm has a unique observer coordinate system with the orientations of each observer coordinate system being dependent on the orientation of the observer reference structure and the orientation of the tool of the respective robotic arm. In some embodiments, although the multiple observer coordinate systems may vary in orientation, all will have the X-axis of its respective observer coordinate system aligned such that its projection in the X-Y plane of the reference structure coordinate system is parallel to and pointing in the same direction as the X-axis of the reference structure coordinate system. FIG. 8 illustrates a dual-arm configuration (medical robotic arm 100 and second medical robotic arm 101) having (1) observer coordinate system 250 aligned to tool axis 460 of tool 400 with the X-axis of observer coordinate system 250 aligned with its projection in the X-Y plane of reference structure coordinate system 210 parallel to and pointing in the same direction as the X-axis of reference structure coordinate system 210, and (2) observer coordinate system 251 aligned to tool axis 461 of tool 401, with the X-axis of observer coordinate system 251 aligned with its projection in the X-Y plane of reference structure coordinate system 210 parallel to and pointing in the same direction as the X-axis of reference structure coordinate system 210.

Figure 3:
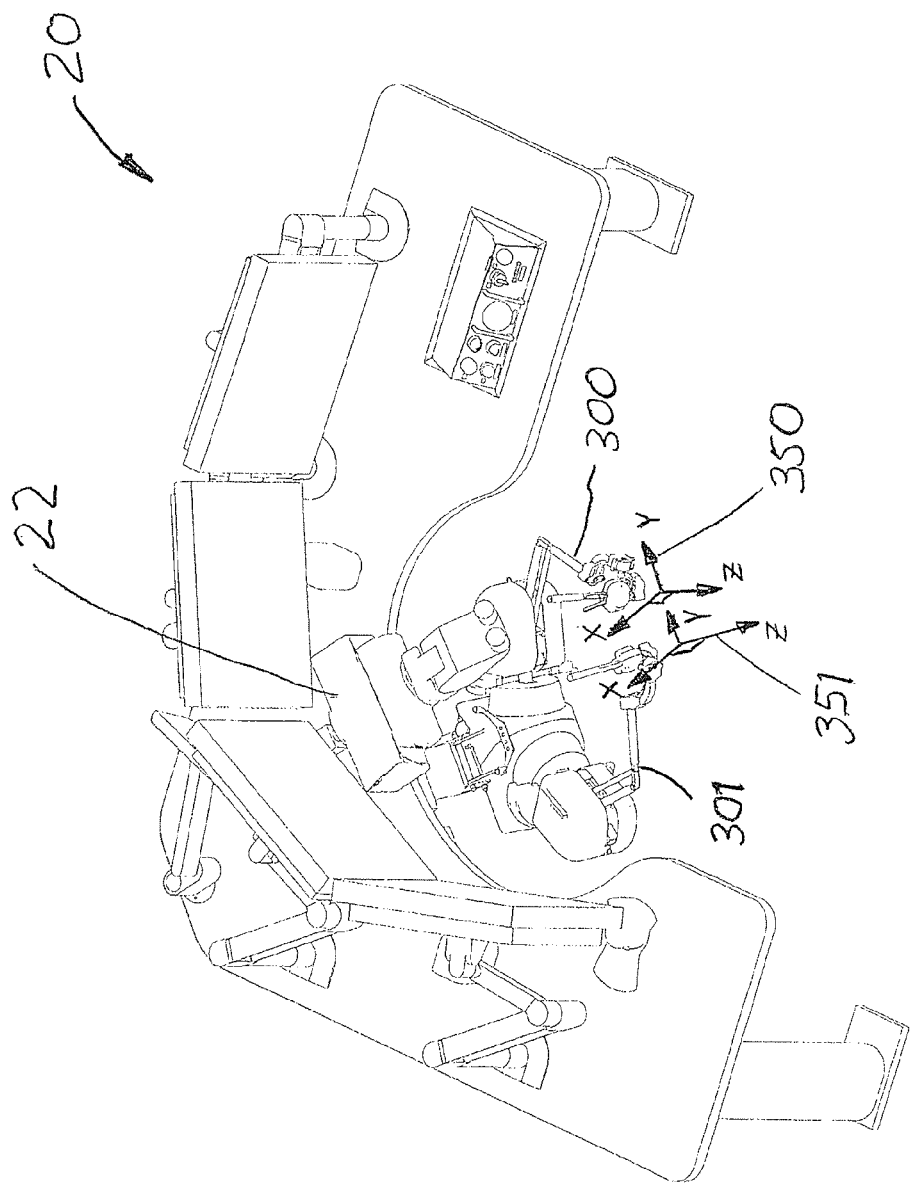
FIG. 3 is a perspective view showing a workstation that may be used by a remote operator to control the robotic system of FIG. 1. Controller device coordinate systems are also depicted.

FIG. 3 shows workstation 20, suitable for use by a remote operator in controlling some embodiments of medical robotic arm 100 and second medical robotic arm 101. Multiple video monitors are available to the operator for viewing information from video cameras, magnetic resonance imagining systems, or other data presenting systems. Viewing instrument 22 may provide a high resolution image from an overhead stereoscopic camera. In some embodiments, viewing instrument 22 is a microscope binocular. Controller device 300 and second controller device 301 provide for the user's input of desired behavior to medical robotic arm 100 and second medical robotic arm 101, respectively. Each controller device is associated with a controller device coordinate system (350, 351).

Figure 4:
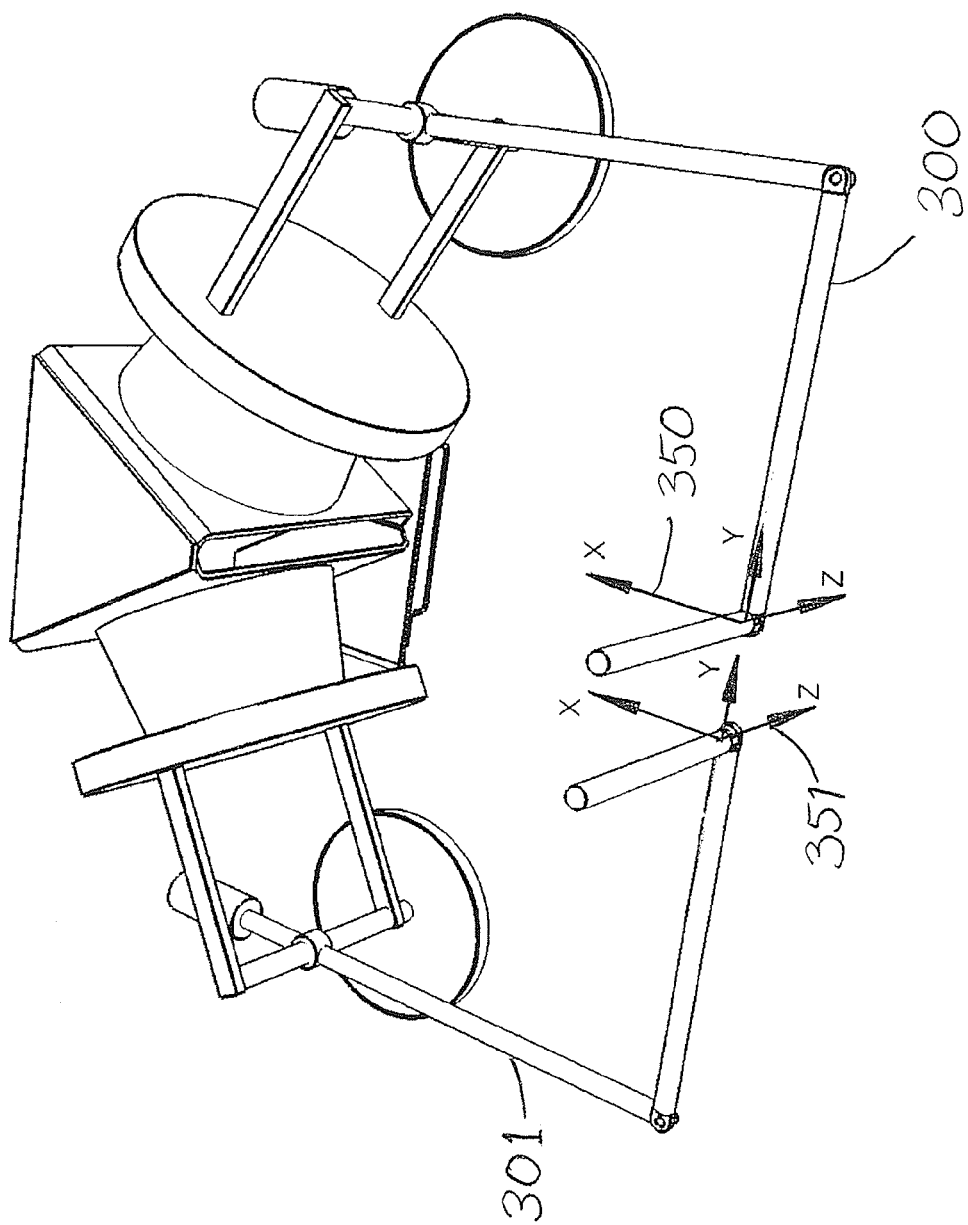
FIG. 4 is a perspective view of a controller device (which is shown as a hand controller) that may be used to control the robotic system of FIG. 1, as well as associated coordinate systems.

FIG. 4 provides another view of an embodiment of controller device 300 and second controller device 301. The Z-axis of controller device coordinate system 350 is aligned with a vertical axis of controller device 300 in the same manner that the Z-axis of observer coordinate system 250 was aligned to tool axis 460 of tool 400. The +X-axis is aligned to point away from the operator, and the orientation of the Y-axis follows convention for right-handed coordinate systems. This alignment of controller device coordinate system 350 results in the X-, Y-, and Z-axes of controller device coordinate system 350, viewed from the perspective of the operator at a workstation, to be identically oriented to the X-, Y-, and Z-axes of observer coordinate system 250, viewed from the perspective of the observer reference structure (see FIG. 6). Because observer coordinate system 250 is fixed to the orientation of the overhead camera that provides the image of the region of interest displayed on viewing instrument 22, the X-, Y-, and Z-axes of controller device coordinate system 350 relate intuitively to the directions seen by the operator when he views the region of interest.

Therefore, input signals to controller device 300 expressed in controller device coordinate system 350 may be directly mapped to a calculated motion of the tool expressed in observer coordinate system 250, and the produced motion will be intuitive to the operator. For example, a motion of +2 (of any unit) in the X-direction of controller device coordinate system 350 generated by an operator moving controller device 300 away from the operator's body may be directly mapped to a calculated motion of tool 400 of +2 (of the same unit) in the X-direction of observer coordinate system 250. Appropriate control signals can be output to actuate robotic arm 100 after solution of the inverse kinematics problem, resulting in motion of tool 400 in a direction directly away from observer reference structure 200. This motion will appear to the operator on viewing instrument 22 as movement of tool 400 towards the top of the screen, corresponding well to the operator's movement of the controller device. Some embodiments may scale the magnitude of the calculated motion (e.g., map to a calculated motion of tool 400 of +1 instead of +2 in the X-direction of observer coordinate system 250 in the example above), while maintaining the same direction.

Figure 5:
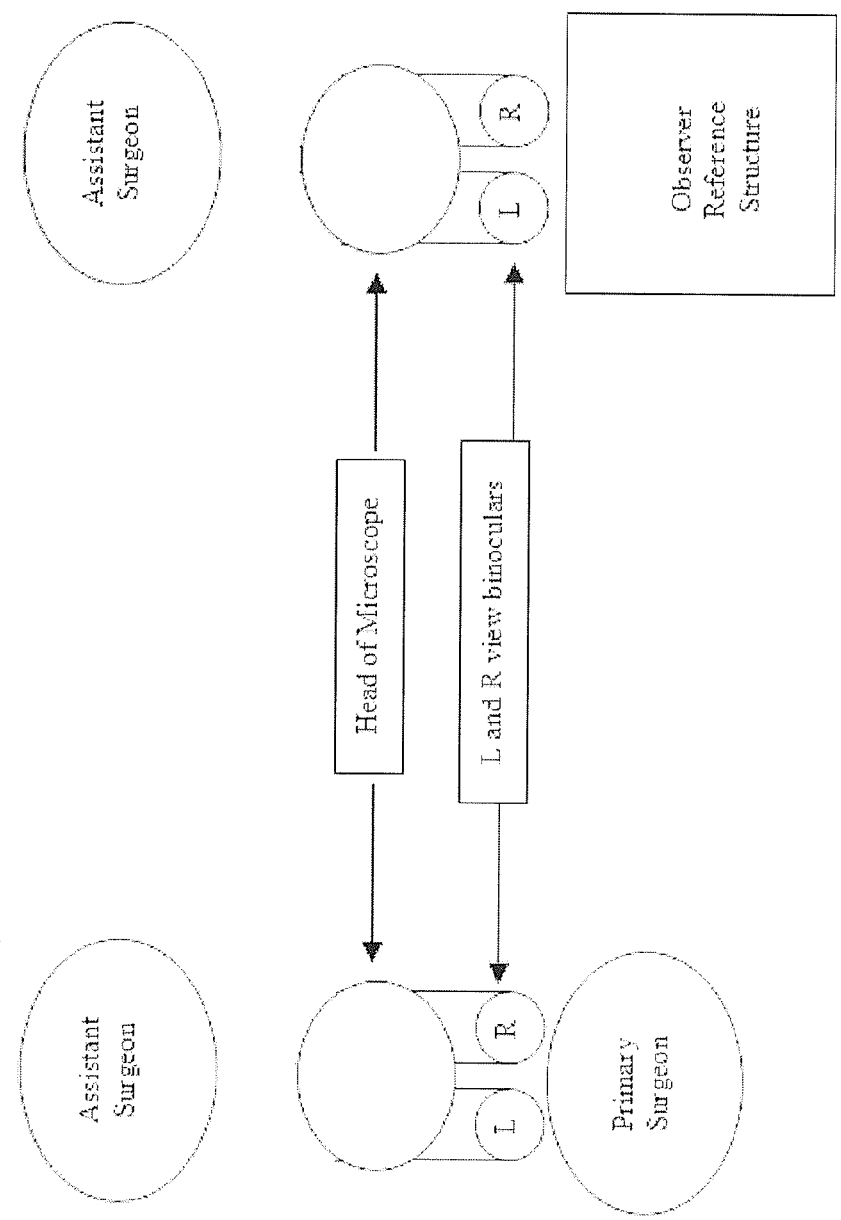
FIG. 5 is a schematic illustration depicting a location for an observer reference structure.
Figure 7:
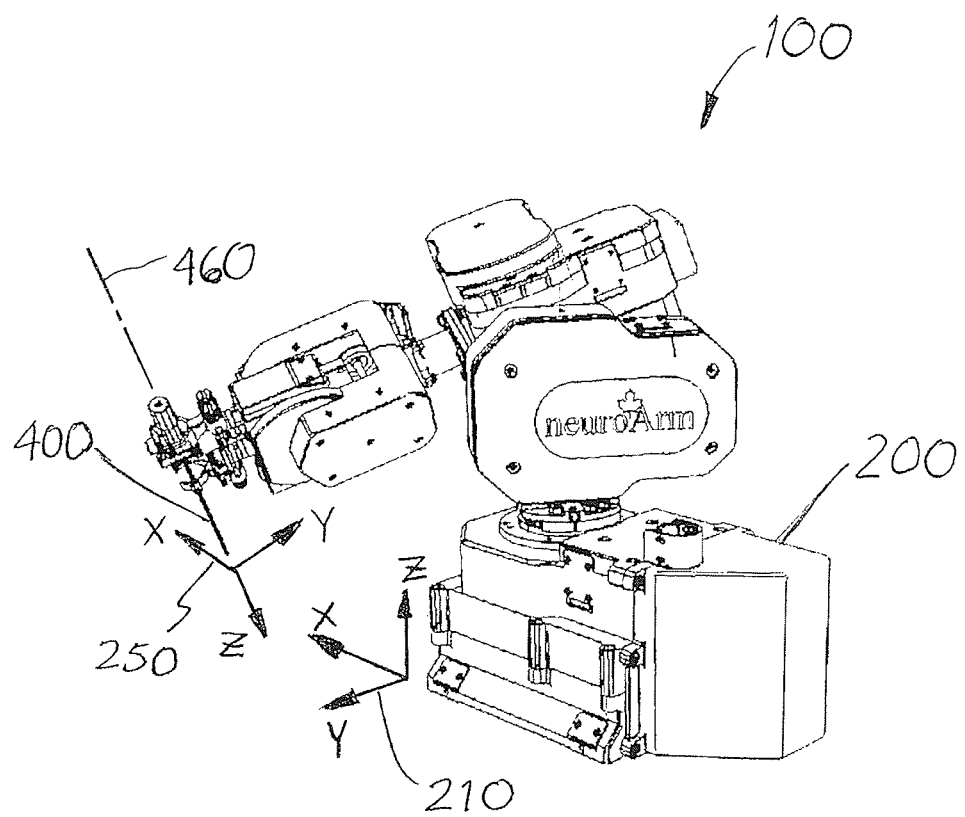
FIG. 7 is a perspective view of a medical robotic arm suitable for use with the present embodiments, depicting the alignment of the observer coordinate system.

FIG. 5 illustrates the intuitive relationship resulting from use of the observer coordinate system and the controller device coordinate system of embodiments of the present techniques. In some embodiments, the observer reference structure is positioned near the patient as if it were a primary surgeon. The positioning of an assistant surgeon may be identical to that taken if a human primary surgeon were present. An operator controlling the robotic system from a remote workstation is presented with the same perspective as a human surgeon manipulating a tool by hand and viewing the region of interest through binoculars that present the surgeon with a left and right view of an image captured by the head of a microscope. The robotic system operator manipulates the tool of the robot through the controller device as if it were a tool directly in front of the operator, and views the region of interest through a microscope binocular viewing system that presents a left and right view captured by a stereoscopic camera (corresponding to the view captured by the human surgeon's microscope).

2.0 Observer Frame Mapping Used with Force Feedback

The determination of coordinate systems described above also is useful in providing force feedback to the operator in an intuitive manner. In some embodiments, measured forces, typically measured in a sensor coordinate system associated with the mounting orientation of the sensor, may be transformed to an expression in the observer coordinate system, then mapped to the controller device coordinate system. The measured forces may be combined with virtual forces, which provide additional information to the operator and may be based on, for example, virtual collisions, joint limits and motion divergence sources.

The control system may be configured to contain three-dimensional models of the robotic arms, tools, and other structures relevant to operator force feedback. In some embodiments, tools may be permitted to collide with one another, but other collisions may be forbidden. If an intended motion will cause collision between the models, manipulator motion is halted and a feedback force is fed back to the controller device in the direction opposite to the commanded motion. Collision detection algorithms are well known in the art, and the use of these algorithms to determine collision avoidance boundaries will be understood by those of ordinary skill. The feedback force applied to the controller device may be proportional to the commanded distance through a collision avoidance boundary. Additional exclusion boundaries that are not associated with physical structures may be modeled and input by the operator.

In some embodiments, joint limits are handled in a similar manner to collisions. When a joint comes to within a specified proximity to a joint limit, manipulator motion is halted and a force is fed back to the controller device in the direction opposite to the commanded motion. The feedback force applied to the controller device may be proportional to the angle by which the commanded joint angle exceeded the limit.

Motion divergence occurs when the actual manipulator position diverges or lags from the commanded position. This can occur if the commanded motion is too fast for the manipulator's actuators to handle, or if something is pushing against the manipulator. In some embodiments, when a divergence between commanded and actual trajectory occurs, a force is fed back to the controller device in the direction opposite to the commanded motion. The feedback force applied to the controller device may be proportional to the divergence error.

In some embodiments, the force feedback applied to the controller device is based on virtual collisions, joint limits, and motion divergence sources. Each virtual force feedback source may be scaled and then summed, or the summed force can be scaled. The control system may be configured to monitor and sum only non-zero values.

Figure 12:
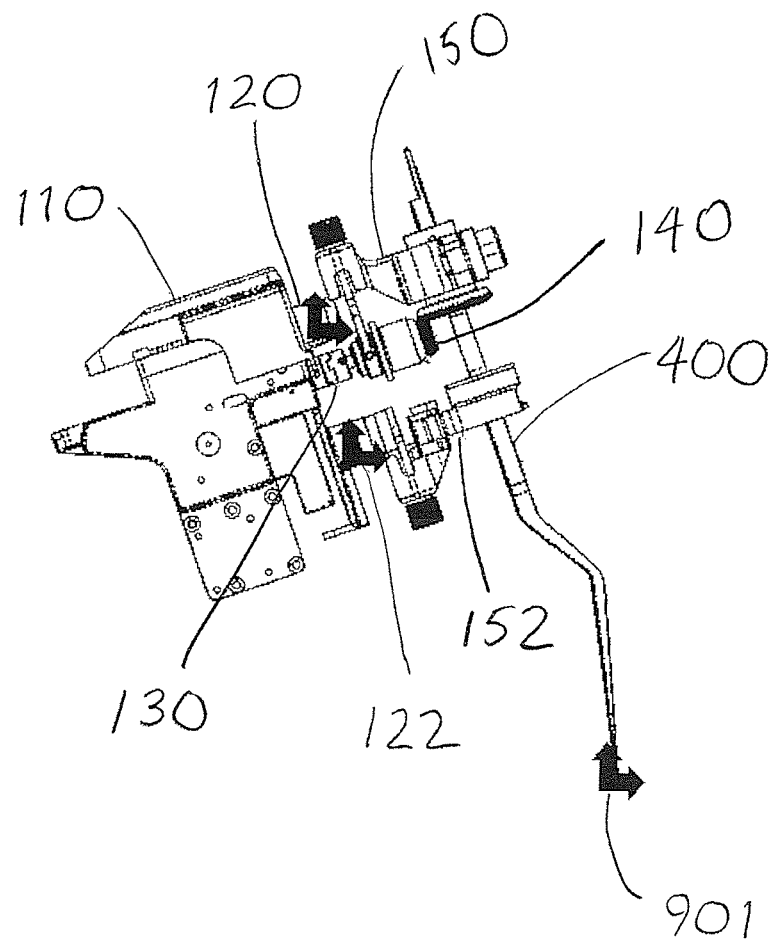
FIG. 12 is a side view of the end effector of FIG. 11 showing tooltip forces that are measured by sensors coupled to the end effector.

FIG. 12 provides a view of a part of a medical robotic arm that is capable of providing measured tooltip forces. Tooltip force 901 acts on tool 400, resulting in forces that can be measured by first sensor 120 and second sensor 122. Tool 400 is held by first tool holder 150 and second tool holder 152, which are coupled to first sensor 120 and second sensor 122, respectively. First sensor 120 and second sensor 122 are mounted to end effector 110. Flexible coupling 130 is also coupled to end effector 110 and provides for actuation of tool 400 via end effector tool actuation gear 140. However, flexible coupling 130 is designed to be compliant in all directions except for rotation about its center axis, and therefore does not transmit any component of tooltip force 901 to end effector 110. Therefore, the entirety of tooltip force 901 is balanced by forces acting through first sensor 120 and second sensor 122, and calculation of tooltip force 901 may be accomplished from the values measured by first sensor 120 and second sensor 122.

Figure 13:
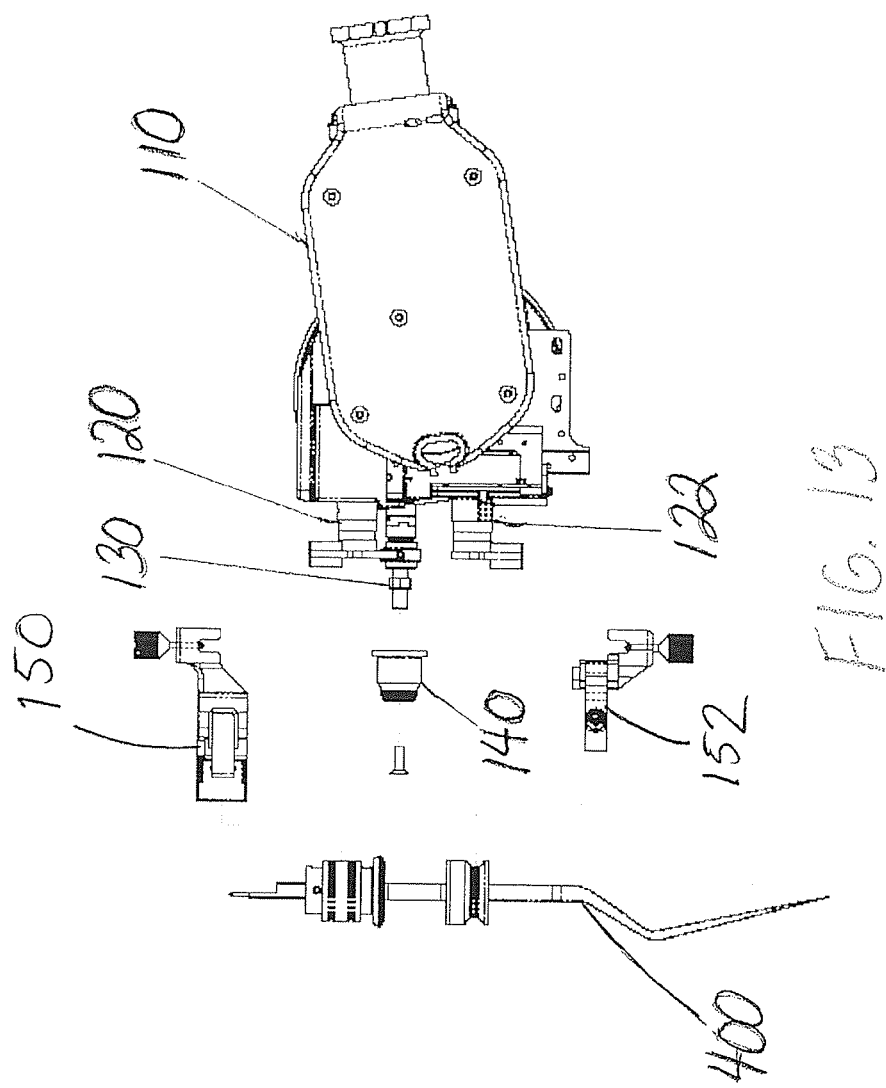
FIG. 13 is an exploded assembly view of the end effector of FIG. 11.

FIG. 13 presents the components described in FIG. 2, depicted in an exploded assembly drawing. In certain embodiments, first sensor 120 and second sensor 122 are six-axis sensors that each use multiple silicon strain gauges inside a cylindrical sensor. First sensor 120 and second sensor 122 may be commercially available force sensors, but compatibility with the magnetic resonance imaging (MRI) environment may limit available candidates or necessitate modification. In some embodiments of medical robotic arms that incorporate the feedback of measured forces, first sensor 120 and second sensor 122 are modified versions of Nano17 Force/Torque sensors from ATI Industrial Automation that have been made to be MR compatible by replacing ferromagnetic materials with titanium.

The measurement and processing of measured forces in some embodiments is as follows:

Each force sensor outputs electrical signals that go through a calibration matrix that is unique to each sensor, the final output being six axes of forces and torques for each sensor. The coordinate orientations of the two force sensor outputs are then aligned so that an X/Y/Z-axis force represents the same direction for each sensor. If the controller devices do not feed torques back to the user, the torques are then disregarded. The forces from the two sensors are then summed to calculate the total actual force; this total actual force is a combination of: bias force, tool and holder gravity forces, tool actuation force, and tooltip forces. These forces are handled as follows:

The bias force may exist due to drift (over time) in the sensors, and may be eliminated after a new tool is scanned. When the stylus is enabled (after tool exchange), the forces from the force sensors are read, and are set to zero. If the tool did not change orientation, this would also eliminate the force due to gravity—however, as the orientation changes, the components of force (X/Y/Z) from gravity on the tool/holders changes, and would cause unwanted force feedback. To avoid this, gravity compensation is used. In the initial position, the force due to gravity is known from the mass of the tool (such as from an initialization file) and the orientation of the tool (from robot kinematics). As the orientation changes, the changes in the calculated gravity force vector are simply added to the sensed forces, eliminating forces due to gravity.

Knowing the mass (from an initialization file) and orientation (from robot kinematics) of the tool and holders, their forces of gravity are mathematically calculated and eliminated so that the user does not feel the weight of the tool/holders, thereby minimizing fatigue and maximizing the sensation from tooltip forces.

Embodiments of the present methods may be coded as software stored on any suitable computer readable media (e.g., tangible computer readable media), such as any suitable form of memory or data storage device, including but not limited to hard drive media, optical media, RAM, SRAM, DRAM, SDRAM, ROM, EPROM, EEPROM, tape media, cartridge media, flash memory, memory stick, and/or the like. Tangible computer readable media includes any physical medium that can store or transfer information. Such embodiments may be characterized as tangible computer readable media having (or encoded with) computer executable (e.g., machine readable) instructions for performing certain step(s). The term "tangible computer readable medium" does not include wireless transmission media, such as carrier waves. The term "computer readable medium," however, does cover wireless transmission media, and some embodiments of the present methods may include wireless transmission media carrying the computer readable instructions described above. The software can be written according to any technique known in the art. For instance, the software may be written in any one or more computer languages (e.g., ASSEMBLY, PASCAL, FORTRAN, BASIC, C, C++, C#, JAVA, Perl, Python) or using scientific packages like, but not limited to, Matlab®, R, S-plus®, and SAS®. The code may be to enable it to be compiled on all common platforms (e.g., Microsoft®, Linux®, Apple Macintosh® OS X, Unix®). Further, well-established cross-platform libraries such as OpenGL® may be utilized to execute embodiments of the present methods, devices and systems. Multi-threading may be used wherever applicable to reduce computing time on modern single- and multi-processor based hardware platforms. As discussed above and illustrated in the figures, the software may include a GUI, which may provide a user with a more intuitive feel when running the software. Different fields may be accessible by screen touching, a mouse and/or keyboard. Alarms, cues, and the like may be done via pop-up windows, audible alerts, or any other techniques known in the art.

Some (up to all) of the steps described in the sections above may be implemented using a computer having a processor (e.g., one or more integrated circuits) programmed with firmware and/or running software. Some (up to all) of the steps described in the sections above may be implemented using a distributed computing environment, which is one example of a computer system (e.g, a control system). In a distributed computing environment, multiple computers may be used, such as those connected by any suitable number of connection mediums (e.g., a local area network (LAN), a wide area network (WAN), or other computer networks, including but not limited to Ethernets, enterprise-wide computer networks, intranets and the Internet, and the connections between computers can be wired or wireless). Servers and user terminals can be part of a given computer system. Furthermore, embodiments of suitable computer systems may be implemented on application specific integrated circuits (ASICs) or very large scale integrated (VLSI) circuits, and further (or alternatively) may be configured to use virtualization of resources, virtual computing, and/or cloud computing to achieve the specified functions. In fact, persons of ordinary skill in the art may utilize any number of suitable structures capable of executing logical operations in order to achieve the functions described above in a computer system consistent with this disclosure.

Descriptions of well known processing techniques, components and equipment have been omitted so as not to unnecessarily obscure the present methods, devices and systems in unnecessary detail. The descriptions of the present methods, devices and systems are exemplary and non-limiting. Certain substitutions, modifications, additions and/or rearrangements falling within the scope of the claims, but not explicitly listed in this disclosure, may become apparent to those of ordinary skill in the art based on this disclosure. Furthermore, it will be appreciated that in the development of a working embodiment, numerous implementation-specific decisions must be made to achieve the developers' specific goals, such as compliance with system-related and business-related constraints, which will vary from one implementation to another. While such a development effort might be complex and time-consuming, it would nonetheless be a routine undertaking for those of ordinary skill in the art having the benefit of this disclosure.

The appended claims are not to be interpreted as including means-plus-function limitations, unless such a limitation is explicitly recited in a given claim using the phrase(s) "means for" and/or "step for," respectively.

The invention claimed is:

1. A method for controlling movement of a robotic arm of a medical robot system, the robotic arm operatively associated with a tool, the medical robot system comprising:
 a medical robot under operator control having at least one robotic arm,
 a camera configured to provide an image of the tool, and
 a reference structure having a fixed orientation relative to the camera, the method comprising:
 a. receiving an input value from a controller device representative of a desired motion of the tool, wherein the input value is expressed in a controller device coordinate system;
 b. determining a calculated motion of the tool based on the input value,
  wherein the calculated motion is expressed in an observer coordinate system that comprises a first axis oriented in fixed relation with an axis of the tool and a second axis oriented orthogonal to the first axis and such that its projection into a plane defined by X and Y axes of an orthogonal coordinate system defined relative to the reference structure is parallel to and pointing in the same direction as the X axis;
 c. determining a commanded motion of the robotic arm based on the calculated motion and the position of the robotic arm; and
 d. outputting an actuation signal to move the robotic arm in accordance with the commanded motion.

2. The method of claim 1, wherein:
 the input value can be expressed in the controller device coordinate system as an input vector having an input magnitude and an input direction;
 the calculated motion can be expressed in the observer coordinate system as a calculated motion vector having a calculated motion magnitude and a calculated motion direction; and
 the calculated motion direction equals the input direction.

3. The method of claim 1, further comprising:
 determining a calculated observer force value that is expressed in the observer coordinate system and based on a virtual force value; and outputting a feedback signal to the controller device in accordance with the calculated observer force value.

4. The method of claim 3, wherein calculation of the virtual force value comprises using one or more calculated virtual collisions, one or more joint limits, motion divergence, or a combination thereof.

5. The method of claim 1, further comprising:
determining a calculated observer force value that is expressed in the observer coordinate system and based on a measured force value from the robotic arm; and
outputting a feedback signal to the controller device in accordance with the calculated observer force value.

6. The method of claim 5, wherein the measured force value is representative of a force measured at a location on the robotic arm and expressed in a sensor coordinate system and wherein the determining of the calculated observer force value is based on the measured force value and the position of the robotic arm.

7. The method of claim 5, wherein the calculated observer force value is also based on a virtual force value.

8. The method of claim 1, wherein the medical robot comprises two robotic arms, each operatively associated with a tool, and the method further comprises:
receiving a second input value from a second controller device representative of a second desired motion of a second tool, wherein the second input value is expressed in a second controller device coordinate system;
determining a second calculated motion of a second tool based on the second input value, wherein the second calculated motion is expressed in a second observer coordinate system that comprises a first axis oriented in fixed relation with an axis of the second tool and a second axis oriented orthogonal to the first axis and such that its projection into a plane defined by X and Y axes of the orthogonal coordinate system defined relative to the reference structure is parallel to and pointing in the same direction as the X axis;
determining a second commanded motion of the second robotic arm based on the second calculated motion and the position of the second robotic arm; and
outputting a second actuation signal to move the second robotic arm in accordance with the second commanded motion.

9. The method of claim 8, further comprising:
determining a second calculated observer force value that is expressed in the second observer coordinate system and based on a second virtual force value, and
outputting a second feedback signal to the controller device in accordance with the second calculated observer force value.

10. The method of claim 9, wherein calculation of the second virtual force value comprises using one or more calculated virtual collisions, one or more joint limits, motion divergence, or a combination thereof.

11. The method of claim 8, further comprising:
determining a second calculated observer force value that is expressed in the second observer coordinate system and based on a second measured force value from the second robotic arm, and
outputting a second feedback signal to the controller device in accordance with the second calculated observer force value.

12. The method of claim 11, wherein the second measured force value is representative of a force measured at a location on the second robotic arm and expressed in a sensor coordinate system and wherein the determining of the second calculated observer force value is based on the second measured force value and the position of the second robotic arm.

13. The method of claim 11, wherein the second calculated observer force value is also based on a second virtual force value.

14. The method of claim 1, wherein the observer coordinate system further comprises a third axis orthogonal to both the first axis and the second axis.

15. The method of claim 14, wherein the controller device coordinate system comprises three orthogonal axes, and wherein the input value received from the controller device is directly mapped to the calculated motion of the tool.

16. The method of claim 14, wherein the controller device coordinate system comprises three orthogonal axes, and wherein each axis of the controller device coordinate system, viewed from an operator perspective, is identically oriented to a corresponding axis of the observer coordinate system, viewed from a perspective of the reference structure.

17. A computer readable medium comprising machine readable instructions for performing the method according to claim 1.

18. A control system configured to control movement of at least one robotic arm of a medical robot system, the robotic arm operatively associated with a tool, the medical robot system comprising:
a medical robot under operator control having at least one robotic arm,
a camera configured to provide an image of the tool, and
a reference structure having a fixed orientation relative to the camera,
the control system comprising:
a computing device operatively associated with the medical robot, wherein the computing device is configured to receive an input value from a controller device representative of a desired motion of the tool, wherein the input value is expressed in a controller device coordinate system; determine a calculated motion of the tool based on the input value, wherein the calculated motion is expressed in an observer coordinate system that comprises a first axis oriented in fixed relation with an axis of the tool and a second axis oriented orthogonal to the first axis and such that its projection into a plane defined by X and Y axes of an orthogonal coordinate system defined relative to the reference structure is parallel to and pointing in the same direction as the X axis; determine a commanded motion of the robotic arm based on the calculated motion and the position of the robotic arm; and output an actuation signal to move the robotic arm in accordance with the commanded motion, and
at least one controller device operatively associated with the computing device and configured to receive an input of a desired movement of the robotic arm.

19. The control system according to claim 18, further comprising a viewing instrument configured to display the image of the tool.

* * * * *

UNITED STATES PATENT AND TRADEMARK OFFICE
CERTIFICATE OF CORRECTION

| | | |
|---|---|---|
| PATENT NO. | : 8,554,368 B2 | Page 1 of 1 |
| APPLICATION NO. | : 12/596417 | |
| DATED | : October 8, 2013 | |
| INVENTOR(S) | : Fielding et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this
Third Day of March, 2015

Michelle K. Lee
*Deputy Director of the United States Patent and Trademark Office*